US00PP15015P2

(12) United States Plant Patent
Redman

(10) Patent No.: US PP15,015 P2
(45) Date of Patent: Jul. 13, 2004

(54) CHRYSANTHEMUM PLANT NAMED 'TEXAS TIME RED'

(50) Latin Name: *Chrysanthemum morifolium*
Varietal Denomination: Texas Time Red

(75) Inventor: Ruth Redman, Bognor Regis (GB)

(73) Assignee: Cleangro LTD (GB)

( * ) Notice: Subject to any disclaimer, the term of this patent is extended or adjusted under 35 U.S.C. 154(b) by 0 days.

(21) Appl. No.: 10/364,266

(22) Filed: Feb. 10, 2003

(51) Int. Cl.[7] ..... A01H 5/00
(52) U.S. Cl. ..... Plt./286
(58) Field of Search ..... Plt./286, 298

(56) References Cited

PUBLICATIONS

Brummitt, Dick, Chrysanthemum once again, 1997, The Garden, pp. 662–663.*
1998 Ficor catalog, listing the variety 'Pixie Time Pink.' See, e.g., p. 4.
1999 Ficor catalog, listing the variety 'Pixie Time Pink.' See, e.g., p. 4.
2000 Ficor catalog, listing the variety 'Pixie Time Pink.' See, e.g., p. 4.
2001 Ficor catalog, listing the varieties 'Pixie Time Pink,' 'Bi Time Purple' and 'Energy Time.' See, e.g., p. 4.
2002 Ficor catalog, listing the variety 'Bi Time Purple' and 'Energy Time.' See, e.g., p. 4.
U.S. Plant Patent Application Publication No. US 2002/0129418 P1, pub. date Sep. 12, 2002, U.S. plant application Ser. No. 09/802,056 filed Mar. 7, 2001, for variety 'Energy Time,' Inventor Mark Roland Boeder.

* cited by examiner

*Primary Examiner*—Anne Marie Grunberg
*Assistant Examiner*—June Hwu
(74) *Attorney, Agent, or Firm*—Howrey Simon Arnold & White, LLP

(57) ABSTRACT

A new variety of Chrysanthemum plant named 'Texas Time Red,' having a good uniform canopy of red single quill with red spoon tip flowers and a light green disc. The new variety has a medium tall vigor, free branching, uniform spreading habit and good foliage presentation.

1 Drawing Sheet

Latin name of the genus and species: Botanical classification: *Chrysanthemum morifolium.*

Variety denomination: The new Chrysanthemum variety denomination is 'Texas Time Red.'

BACKGROUND OF THE INVENTION

The present invention comprises a new and distinct cultivar of Chrysanthemum botanically known as *Chrysanthemum morifolium,* and referred to by the cultivar name 'Texas Time Red.'

'Texas Time Red,' identified as 21895-0, originated from a cross made in a controlled breeding program in Vinnetrow Road, Chichester, West Sussex, United Kingdom. The female parent of the new variety is an undistributed, unpatented seedling identified as 21079-4 of the unpatented variety known as 'Pixie Time Pink.' The male parent of the new variety is an undistributed, unpatented seedling identified as 20074-2 of the unpatented variety known as 'Bi Time Purple.' The new variety 'Texas Time Red' has been asexually reproduced by vegetative cuttings in Chichester, West Sussex, United Kingdom and the distinguishing characteristics are retained through successive generations of asexual reproduction.

BRIEF SUMMARY OF THE INVENTION

'Texas Time Red' is a Pot type of Chrysanthemum plant variety having red single quill flowers with red spoon tips.

Comparison with Female Parent

Plants of the new Chrysanthemum variety 'Texas Time Red' are dissimilar to the parent 'Pink Pixie Time' in plant habitat and growth rate. In side-by-side comparisons in Chichester, West Sussex, United Kingdom, under commercial practice, plants of the new Chrysanthemum variety 'Texas Time Red' differed from the plants of the parent 'Pixie Time Pink' in the following characteristics.

1. The new variety 'Texas Time Red' produces red quill single spoon tipped flowers whereas the parent 'Pixie Time Pink' produces pink anemone flowers.
2. Plants of the new variety 'Texas Time Red' have taller and larger inflorescence than plants of the parent 'Pixie Time Pink.'

Comparison with Male Parent

Plants of the new Chrysanthemum variety 'Texas Time Red' are dissimilar to the parent 'Bi Time Purple' in plant habitat and growth rate. In side-by-side comparisons in Chichester, West Sussex, United Kingdom, under commercial practice, plants of the new Chrysanthemum variety 'Texas Time Red' differed from the plants of the parent 'Bi Time Purple' in the following characteristics.

1. The new variety 'Texas Time Red' produces red quill single spoon tipped flowers whereas the parent 'Bi Time Purple' produces purple anemone flowers.
2. Plants of the new variety 'Texas Time Red' have tall and larger inflorescence than plants of the parent 'Bi Time Purple.'

Comparison with Other Varieties

Plants of the new Chrysanthemum variety 'Texas Time Red' are similar to 'Energy Time' (U.S. Plant Pat. No.

13,957) in plant habit and growth rate. However in side-by-side comparisons in Chichester, West Sussex, United Kingdom, under commercial practice, plants of the new Chrysanthemum variety 'Texas Time Red' differed from plants of 'Energy Time' in the following characteristics.

1. The new variety 'Texas Time Red' produces dark red quill single spoon tip flowers whereas 'Energy Time' produces red spoon tip flowers.
2. Plants of the new variety 'Texas Time Red' have larger and taller inflorescence than plants of 'Energy Time.'

BRIEF DESCRIPTION OF ILLUSTRATION

Typical specimens of the plant and flowers for the new Chrysanthemum variety 'Texas Time Red' are shown in the accompanying digital photograph. The colors shown are as true as possible within the usual limits of this kind of illustration.

FIG. 1 is a whole plant view of the new variety 'Texas Time Red' grown in a pot. The plant shown in the illustration is 58 days from the commencement of Short Days.

DETAILED BOTANICAL DESCRIPTION

The following description of the new Chrysanthemum variety 'Texas Time Red' is of plants grown in a greenhouse in Chichester, West Sussex, United Kingdom in the month of May. The cultivar has not been observed under all possible environmental conditions. The phenotype may vary significantly with variations in the environment such as temperature, length of day and light intensity, without any variance in genotype. The commercial classification of the new variety is a pot Chrysanthemum.

Plants of the new variety have been grown successfully under temperature conditions averaging about 19° C. at night and about 17° C. to 24° C. during the day under light conditions of about 5000 to 6000 foot candles. The plants respond well to the use of growth retardant, such as B9 treatment at about 2 g per liter. To produce a commercial product the plants may be pinched once with the center bud removed. The typical container size for commercial growth is 1 liter. It has been observed that the shelf life of the new variety is about 25 days with a response time of about 8 weeks. The new variety is suitable for growth in a temperature range of 15° C. to 25° C.

The new variety may be produced as a spray. The following description is with respect to a plant produced as a pot. In the description of this new Chrysanthemum variety, color values have been taken from The Royal Horticultural Society Colour Chart (R.H.S.C.C.).

Plant

Plant type: Pot.
Habit: Upright and free branching.
Height: 22 cm.
Width: 32 cm.
Branching characteristics: Upright and free branching.
Length of lateral branches: 19 cm.
Number of breaks from pinch: 7.
Stem color: 138B.
Response time: 56 days.
Vigor: Medium Tall.
Shelf life: 25 days.
Disease/(susceptibility/resistance observed): None observed to date.
Growth retardant type and treatment: 3 applications of 2.5 gm/liter B9 @ 2, 21 and 28 days after sticking unrooted cuttings.

The plants were grown for 2 weeks in Long Day conditions (20 hours of light) and then transferred to Short Day conditions (13 hours of dark).

Propagation:
*Type.*—Vegetative propagation via stem cuttings.
*Time to rooting.*—14 days with soil temperatures of 18° C.
*Rooting habit.*—After 7 Long Days the first roots emerge and form root primordia. In 14 days a complete root system is developed.

Foliage

Number of leaves per lateral branch: 10.
Compound or single: Single.
Arrangement of leaves: Alternate.
*Shape of leaf.*—Typically 5 lobed ovate.
*Size of leaf.*—Width (cm): 4.5. Length (cm): 2.5.
*Leaf apex.*—Acute.
*Base.*—Obtuse.
*Attachment.*—Petioled.
*Aspect.*—Slight undulating.
*Margin.*—Palmately lobed.
*Surface characteristics.*—Top: slightly pubescent. Bottom: pubescent.
Petiole:
*Color.*—137B.
*Length.*—2.5 cm.
*Diameter.*—0.2 cm.
Venation: Net prominent mid-vein at underside.
*Color.*—Upper side: near 137C. Under side: near 138B.
Color:
*Mature leaf, upper side.*—Near 137A; under side: near 138B.
*Young leaf, upper side.*—Near 147A; under side: near 137A.

Flower

Flower appearance: Matte.
Flower type: Single.
Flower form: Slightly cupped.
Flower shape: Round.
Flowering habit: Cyne.
Number of blossoms per branch: 5.
Inflorescence form: Cyme.
*Depth of fully expanded blossoms.*—2 cm.
*Diameter of fully expanded blossoms.*—5.5 cm.
Phyllaries:
*Number.*—15.
*Color.*—Near 139C.
*Length.*—0.7 cm.
*Width.*—0.1 cm.
*Texture/appearance.*—Pubescent.
Peduncle: peduncle length is shortest at the terminal flower and progressively longer moving down the stem.
*Length.*—12 cm.
*Color.*—Near 138C.
*Surface.*—Pubescent.
*Habit.*—Slightly undulating.
*Strength.*—Medium.
Pedicel:
*Length.*—Terminal: 4 cm; lateral: 5 cm.

*Color.*—Near 138C.
*Surface.*—Pubescent.
*Habit.*—Slightly undulating.
*Strength.*—Medium.

Ray florets:
*Form/shape.*—Straight and cylindrical.
*Texture/appearance.*—Matte.
*Number per flower.*—44.
*Length.*—3.5 cm; Width: 0.5 cm.
*Apex.*—Rounded.
*Base.*—Tapered.
*Margin.*—Entire.

Disc florets:
*Form/shape.*—Cylindric.
*Texture/appearance.*—Shiny.
*Number per flower.*—135.
*Length.*—0.6 cm; Width: 0.1 cm.
*Diameter of disc.*—1.5 cm.

Fragrance: None.

Flower bud (at onset of color):
*Length.*—1.5 cm.
*Diameter.*—1 cm.
*Form/shape.*—Domed.

General flower color:
1. *Ray florets, upper side.*—45A and near 22C. Immature: near 46A and near 22C. Mature: near 45A and outer tube near 22C. Older/Fading: near 45B and outer tube near 22C.
2. *Ray florets, under side.*—45A. Immature: near 45A. Mature: near 45A. Older/Fading: Near 44A.
3. *Disc florets.*—Immature: near 151A. Mature: near 151B. Older/Fading: near 151B.
4. *Bud.*—45A.

Flower progression with age: Flower form does not change but there is a little fading with age.

Lastingness of blooms: Shelf life of blooms is about 25 days.

Reproductive Organs

Gynoecium: Present on Ray and Disc florets.

Ray florets per individual flower:
*Pistil number.*—44.
*Stigma color.*—Near 154A.
*Stigma shape.*—Forked.
*Style color.*—Near 154B.
*Style length.*—0.3 cm.

Disc florets per individual flower:
*Pistil number.*—135.
*Stigma color.*—Near 154A.
*Stigma shape.*—Forked.
*Style color.*—Near 154B.
*Style length.*—0.3 cm.

Androecium: Not observed.

Fruit and seeds: None observed.

What is claimed is:

1. A new and distinct variety of Chrysanthemum plant, substantially as described and illustrated herein.

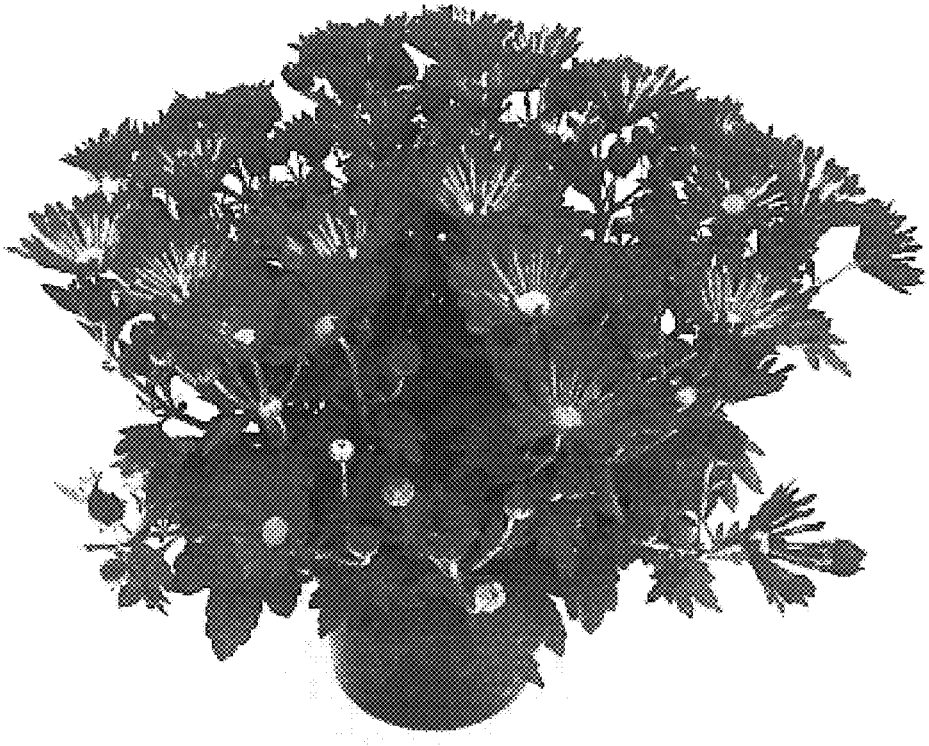

* * * * *